US010550414B2

(12) United States Patent
Kim et al.

(10) Patent No.: US 10,550,414 B2
(45) Date of Patent: Feb. 4, 2020

(54) COMPOSITION FOR PRODUCING D-PSICOSE COMPRISING D-PSICOSE 3-EPIMERASE AND SALT AND METHOD FOR PRODUCING D-PSICOSE USING SAME

(71) Applicant: CJ CHEILJEDANG CORPORATION, Seoul (KR)

(72) Inventors: Jung Eun Kim, Bucheon (KR); Yang Hee Kim, Suwon (KR); Seong Bo Kim, Seongnam (KR); Seung Won Park, Yongin (KR); Ji Hyun Kang, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 11 days.

(21) Appl. No.: 16/065,749

(22) PCT Filed: Dec. 23, 2016

(86) PCT No.: PCT/KR2016/015250
§ 371 (c)(1),
(2) Date: Jun. 22, 2018

(87) PCT Pub. No.: WO2017/111563
PCT Pub. Date: Jun. 29, 2017

(65) Prior Publication Data
US 2019/0136276 A1    May 9, 2019

(30) Foreign Application Priority Data
Dec. 23, 2015   (KR) ........................ 10-2015-0184869

(51) Int. Cl.
*C12N 9/90*     (2006.01)
*C12P 19/02*    (2006.01)
(Continued)

(52) U.S. Cl.
CPC ................ *C12P 19/02* (2013.01); *C12N 1/20* (2013.01); *C12N 9/1205* (2013.01); *C12N 9/90* (2013.01);
(Continued)

(58) Field of Classification Search
None
See application file for complete search history.

(56) References Cited

U.S. PATENT DOCUMENTS 3,256,270 A    6/1966   Erich et al.
8,030,035 B2   10/2011  Oh et al.
(Continued)

FOREIGN PATENT DOCUMENTS

JP        2876416 B2      3/1999
JP      2008541753 A     11/2008
(Continued)

OTHER PUBLICATIONS

International Search Report for International Patent Application No. PCT/KR2016/015250, dated Mar. 29, 2017.
(Continued)

*Primary Examiner* — Rebecca E Prouty (57) ABSTRACT

The present application relates to a composition for producing D-psicose comprising (a) a D-psicose 3-epimerase, a strain expressing the enzyme or a culture of the strain, and (b) at least one salt selected from the group consisting of an aluminate and an iodate, and a method for producing D-psicose from D-fructose or a method for increasing the conversion of D-fructose into D-psicose comprising adding (b) to (a).

4 Claims, 4 Drawing Sheets

Specification includes a Sequence Listing.

(51) Int. Cl.
    *C12P 19/24*     (2006.01)
    *C12N 1/20*     (2006.01)
    *C12N 9/12*     (2006.01)
    *C12R 1/15*     (2006.01)

(52) U.S. Cl.
    CPC ............... *C12P 19/24* (2013.01); *C12R 1/15* (2013.01); *C12Y 207/01101* (2013.01)

(56) References Cited

U.S. PATENT DOCUMENTS

| | | |
|---|---|---|
| 8,735,106 B2 | 5/2014 | Hong et al. |
| 2010/0190225 A1 | 7/2010 | Oh et al. |
| 2012/0244580 A1 | 9/2012 | Hung et al. |

FOREIGN PATENT DOCUMENTS

| | | |
|---|---|---|
| JP | 2013501519 A | 1/2013 |
| KR | 1019890009958 A | 8/1989 |
| KR | 1020060125971 A | 12/2006 |
| KR | 101106253 B1 | 1/2012 |
| KR | 101539096 B1 | 7/2015 |

OTHER PUBLICATIONS

Arthur J. Shaw, III, and George T. Tsao, "Isomerization of D-Glucose With Sodium Aluminate: Kinetics as a Function of Temperature", 1978, vol. 60, p. 376-382, Carbohydrate Research.

Arthur J. Shaw, III, and George T. Tsao, "Isomerization of D-Glucose With Sodium Aluminate: Mechanism of the Reaction", 1978, vol. 60, p. 327-335, Carbohydrate Research.

INDICATIONS RELATING TO DEPOSITED MICROORGANISM
OR OTHER BIOLOGICAL MATERIAL (PCT Rule 13bis)

A. The indications made below relate to the deposited microorganism or other biological material referred to in the description
on page 17, line 74.

B. IDENTIFICATION OF DEPOSIT

Name of depositary institution
Korean Culture Center of Microorganisms (KCCM)

Address of depositary institution (including postal code and country)
120-861, Yurim Building, Hongjenae-2ga-gil 45, Seodaemun-Gu, Seoul, Korea Date of deposit: October 20, 2016  Accession Number: KCCM11918P

C. ADDITIONAL INDICATIONS

D. DESIGNATED STATES FOR WHICH INDICATIONS ARE MADE

E. SEPARATE FURNISHING OF INDICATIONS

COMPOSITION FOR PRODUCING D-PSICOSE COMPRISING D-PSICOSE 3-EPIMERASE AND SALT AND METHOD FOR PRODUCING D-PSICOSE USING SAME

CROSS-REFERENCE TO RELATED APPLICATION

This application is a U.S. National Stage of International Patent Application No. PCT/KR2016/015250, filed on Dec. 23, 2016, which claims priority to Korean Patent Application No. 10-2015-0184869, filed on Dec. 23, 2015, which are hereby incorporated by reference in their entirety.

TECHNICAL FIELD

The present invention relates to a composition for producing D-psicose comprising a D-psicose 3-epimerase and a salt, and a method for producing D-psicose using the composition.

BACKGROUND ART

D-psicose is a natural sugar present in a trace amount in fruits such as figs and raisins or isomerization products of molasses or glucose. D-psicose is a monosaccharide with a sweetness of 70% relative to sugar. D-psicose was reported to be a sweetener that contains few or no calories because it is not metabolized and that has little effect on body weight gain because it functions to inhibit the formation of body fat. D-psicose was also reported to inhibit the activity of enzymes involved in lipid synthesis, resulting in a reduction in abdominal obesity (Matuo, T. et al., Asia Pac. J. Clin. Nutr., 10, 223-237, 2001; Matsuo. T. and K. Izumori. AsiaPac. J. Clin. Nutr., 13, 5127, 2004). According to a recently published report, D-psicose has no influence on hyperglycemia and assists in dental health due to its non-cariogenic and anti-cariogenic properties.

Thus, D-psicose has attracted increasing attention as a sweetener due to advantages thereof. However, since D-psicose is a rare monosaccharide that exists only in a trace amount in nature, there is a need to develop an efficient technique for D-psicose production that can be applied to the food industry.

Conventional methods for D-psicose production are divided into chemical methods and biological methods. According to the chemical methods, psicose is produced from fructose based on the catalysis of molybdate ions. The chemical methods are disadvantageous in that D-psicose is produced in a very small amount during treatment of molasses or isomerization of glucose, considerable costs are incurred, and large amounts of by-products are generated. According to the biological methods, D-psicose is produced from D-fructose using a D-psicose 3-epimerase. Problems of the biological methods are very low yields and high production costs.

In an effort to solve such problems, the present inventors reported a method for economically producing D-psicose comprising isomerizing glucose to fructose and reacting the fructose with immobilized bacterial cells producing a D-psicose 3-epimerase (Korean Patent Application No. 10-2009-0118465), prior to the filing of the present application. The present inventors also reported a method for economically producing pure D-psicose in a crystalline state without using an organic solvent such as ethanol. D-psicose produced by this method is flowable during production and has commercial value (Korean Patent Application No. 10-2010-0027546).

However, the methods for producing D-psicose using a D-psicose 3-epimerase (also referred to simply as "psicose epimerase") (hereinafter, the methods are referred to simply as "enzymatic conversion methods") are still limited in yield. Thus, an effort needs to be made to increase the yield of D-psicose for industrial mass production and improve the conversion rate of D-fructose to D-psicose by a psicose epimerase to lower production cost.

Under such circumstances, the present inventors have earnestly conducted research to develop a method for improving the conversion rate of D-fructose to D-psicose using a psicose epimerase, and as a result, found that use of an aluminate or iodate in an enzymatic conversion method can significantly improve the conversion rate. The present invention has been accomplished based on this finding.

DISCLOSURE

The Sequence Listing created on Jun. 22, 2018 with a file size of 9.68 KB, and filed herewith in ASCII text file format as the file entitled "4019686.TXT," is hereby incorporated by reference in its entirety.

Technical Problem

It is one object of the present invention to provide a composition for producing D-psicose comprising (a) a D-psicose 3-epimerase, a strain expressing the enzyme or a culture of the strain and (b) at least one salt selected from the group consisting of aluminates and iodates.

It is another object of the present invention to provide a method for producing D-psicose from D-fructose comprising adding (b) at least one salt selected from the group consisting of aluminates and iodates to (a) a D-psicose 3-epimerase, a strain expressing the enzyme or a culture of the strain.

It is a further object of the present invention to provide a method for increasing the conversion rate of D-fructose to D-psicose using a D-psicose 3-epimerase comprising adding (b) at least one salt selected from the group consisting of aluminates and iodates to (a) a D-psicose 3-epimerase, a strain expressing the enzyme or a culture of the strain.

Technical Solution

In order to achieve the above and other objects of the present invention, one aspect of the present invention provides a composition for producing D-psicose comprising (a) a D-psicose 3-epimerase, a strain expressing the enzyme or a culture of the strain and (b) at least one salt selected from the group consisting of aluminates and iodates.

The D-psicose 3-epimerase (hereinafter referred to simply as "psicose epimerase") used in the composition of the present invention may be any protein that is active in the epimerization of D-fructose to D-psicose. A strain endogenously expressing the protein, a transformant of the strain expressing the protein, a culture of the strain or a protein isolated from the culture may be used as the psicose epimerase.

In one embodiment, the psicose epimerase may be a wild-type psicose epimerase derived from *Agrobacterium tumefaciens* or *Kaistia granuli* or a variant thereof. Specifically, the psicose epimerase may be one that has a homology of at least 70%, at least 80%, at least 90%, at least 95%, at least 97%, at least 99% or 100% to the amino acid sequence set forth in SEQ ID NO: 1, 2, 3 or 4. A psicose epimerase variant whose amino acid sequence has a homology to the amino acid sequence set forth in SEQ ID NO: 1, 2, 3 or 4 and is partially deleted, modified, substituted or added is also within the scope of the present invention as long as its amino acid sequence is enzymatically active in epimerizing D-fructose to D-psicose. More specifically, the psicose epimerase may have the amino acid sequence set forth in SEQ ID NO: 1 or 4.

As used herein, the term "homology" refers to a percentage of identity between two polypeptide moieties. The correspondence between the sequences from one moiety to another can be determined by techniques known in the art. For example, the homology may be determined by aligning sequence information and directly aligning the sequence information between two polypeptide molecules using a readily available computer program. The homology may also be determined by hybridizing polynucleotides under conditions where stable double strands between homologous regions are formed, degrading the hybridized polynucleotides with a single-stranded-specific nuclease, and determining the size of the degraded fragments.

As used herein, the term "homologous" in all its grammatical forms and spelling variations refers to the relationship between proteins that possess a "common evolutionary origin," comprising proteins from superfamilies (e.g., the immunoglobulin superfamily) and homologous proteins from different species (e.g., myosin light chain, etc.). Such proteins (and their encoding genes) have sequence homology, as reflected by their sequence similarity. However, in common usage and in the present invention, the term "homologous," when modified with an adverb such as "highly," may refer to sequence similarity and may or may not relate to a common evolutionary origin.

As used herein, the term "sequence similarity" refers to the degree of identity or correspondence between nucleic acid or amino acid sequences of proteins that may or may not share a common evolutionary origin. In a specific embodiment, two amino acid sequences are "substantially homologous" or "substantially similar" when at least 70% (75%, 90%, 95%, 96%, 97% or 99% according to one embodiment) of the polypeptides match over the defined length of the amino acid sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art (see, for example, Sambrook et al., 1989, infra).

In a further embodiment, the strain expressing the psicose epimerase used in the present invention may be any microorganism that can express a gene encoding any of the amino acid sequences described herein. Specifically, the strain may be *Corynebacterium glutamicum* (KCCM11046P, Korean Patent Publication No. 10-2011-0035805; KCCM11204P, Korean Patent No. 10-1203856; KCCM11403P, Korean Patent No. 10-1455759; or KCCM11918P, Korean Patent Application No. 10-2016-0152947) but is not limited thereto.

The psicose epimerase may be mixed with D-fructose as a substrate before use. Alternatively, D-fructose may be added to the psicose epimerase or vice versa before use. Alternatively, the enzyme or the strain expressing the enzyme may be immobilized on a support before use. Examples of supports suitable for use in the present invention include, but are not limited to, agar, agarose, k-carrageenan, alginate, and chitosan.

The composition of the present invention may further comprise D-fructose. Specifically, the D-fructose may be used at a concentration of 0.01 M to 10 M, 0.01 M to 5 M, 0.01 M to 3 M, 0.05 M to 10 M, 0.05 M to 5 M, 0.05 M to 3 M, 0.08 M to 10 M, 0.08 M to 5 M, 0.08 M to 3 M or 0.1 M to 2.8 M. The salt may be used in such an amount that the molar concentration (M) ratio of the salt to the D-fructose is in the range of 1:0.01 to 1, 1:0.05 to 1, 1:0.1 to 1, 1:0.1 to 0.8, 1:0.1 to 0.6 or 1:0.2 to 0.6. Within this range, the conversion rate of the D-fructose to D-psicose can be maintained in an optimal range.

The conversion rate of D-fructose to D-psicose can be increased in the presence of the salt by a factor of 1.5 to 5.0, 1.8 to 5.0, 2.0 to 5.0, 1.5 to 3.0, 1.8 to 3.0 or 2.0 to 3.0, compared to in the absence of the salt.

The composition of the present invention may optionally further comprise an additive capable of promoting or assisting in the production of D-psicose. The ingredient is not limited and may be, for example, an metal ion, such as manganese, magnesium, iron, cobalt, and/or aluminum, or a metal salt. The metal salt is selected from the group consisting of $NiSO_4$, $NiCl_2$, $CoCl_2$, $MnCl_2$, $MnSO_4$, $ZnSO_4$, and mixtures thereof. The metal ion or the metal salt may be used at a concentration of 0.5 to 10 mM, 0.5 to 5 mM or 0.5 to 3 mM.

Another aspect of the present invention provides a method for producing D-psicose from D-fructose comprising adding (b) at least one salt selected from the group consisting of aluminates and iodates to (a) a D-psicose 3-epimerase, a strain expressing the enzyme or a culture of the strain. A further aspect of the present invention provides a method for increasing the conversion rate of D-fructose to D-psicose using a D-psicose 3-epimerase comprising adding (b) at least one salt selected from the group consisting of aluminates and iodates to (a) a D-psicose 3-epimerase, a strain expressing the enzyme or a culture of the strain.

Now, a description will be given of the method for producing D-psicose from D-fructose and the method for increasing the conversion rate of D-fructose to D-psicose.

According to one embodiment of the present invention, D-fructose may be produced by hydrolysis of sucrose or isomerization of glucose. That is, D-psicose can be produced using common and inexpensive raw materials such as fructose, sucrose and glucose in high yield, enabling mass production of D-psicose. Specifically, each of the methods may further comprise (pre-a) isomerizing D-glucose to D-fructose prior to step (a). In step (pre-a), a protein may be used that is active in glucose isomerization. Examples of suitable proteins include, but are not limited to, glucose isomerases and phosphoglucose isomerases.

According to one embodiment of the present invention, each of the methods may further comprise (c) adding D-fructose before or after or simultaneously with the addition of the salt. According to one embodiment of the present invention, each of the methods may further comprise adding D-fructose simultaneously with the addition of the salt. Specifically, the salt and D-fructose may be added separately at one time. Alternatively, the salt may be added in admixture with D-fructose.

Each of the methods of the present invention may further comprise (c') adding an additive capable of promoting or assisting in the production of psicose. Specifically, the additive may be a metal ion (e.g., manganese, magnesium, iron, cobalt, and/or aluminum) or a metal salt. More specifically, the metal salt may be selected from the group consisting of NiSO$_4$, NiCl$_2$, CoCl$_2$, MnCl$_2$, MnSO$_4$, ZnSO$_4$, and mixtures thereof. According to one embodiment of the present invention, each of the methods may further comprise (d) epimerizing the D-fructose after step (b), (c) or (c'). The reaction may be carried out at a pH of 7 to 9.0, a pH of 7.5 to 9.0, a pH of 7.8 to 9.0, a pH of 8.0 to 9.0, a pH of 7.5 to 8.5, a pH of 7.8 to 8.5, a pH of 7.8 to 8.3 or a pH of 8.0. The reaction may be carried out at a temperature of 30° C. to 65° C., 40° C. to 65° C., 50° C. to 65° C., 50° C. to 60° C., 53° C. to 57° C. or 55° C. The reaction may be carried out for at least 2 hours, at least 3 hours and/or at most 16 hours, at most 24 hours, at most 36 hours or at most 48 hours.

According to another embodiment of the present invention, each of the methods may further comprise (e) isolating and/or purifying D-psicose after step (b), (c), (c') or (d). There is no particular restriction on the method for purifying D-psicose. D-psicose may be purified by any suitable method known in the art. Non-limiting examples of such purification methods include chromatography, fractional crystallization, ion purification, dialysis, precipitation, adsorption, and electrophoresis, which may be carried out alone or in combination. For example, D-psicose may be purified by chromatography. In this case, the target saccharide may be separated based on differences in binding force between saccharides and metal ions attached to an ionic resin.

Each of the methods according to the present invention may further comprise (f) bleaching and/or demineralizing before or after the purification step. The bleaching and/or demineralizing makes D-psicose purer without impurities.

According to another embodiment of the present invention, each of the methods may further comprise (g) crystallizing D-psicose after step (b), (c), (c'), (d), (e) or (f). Any suitable crystallization method known in the art may be used without particular limitation. For example, D-psicose may be crystallized during cooling. As a result of crystallization, purified D-psicose can be obtained in high yield.

According to one embodiment of the present invention, each of the methods may further comprise concentrating the D-psicose solution before the crystallization. This concentration results in a 2.5- to 3-fold reduction in the concentration of the purified D-psicose and enables more efficient crystallization.

According to another embodiment of the present invention, each of the methods may further comprise (h) reusing D-fructose remaining unreacted after purification step (e) in epimerization step (d) and/or reusing the mother liquor from which the crystal has been separated after crystallization step (g) in purification step (e). This reuse allows the production of D-psicose in higher yield and reduces the amount of wasted D-fructose, thus being economically advantageous.

The method for producing D-psicose from D-fructose and the method for increasing the conversion rate of D-fructose to D-psicose share enzyme, strain, culture, and salt in common with the composition for producing D-psicose, and a description thereof is thus omitted to avoid excessive complexity of the specification.

Advantageous Effects

The use of an enzyme derived from a microorganism makes the method for producing D-psicose environmentally friendly. In addition, the addition of an aluminate or iodate to enhance the conversion rate of D-fructose to D-psicose through an enzymatic reaction significantly increases the production yield of D-psicose, thus being effective in maximizing the production of D-psicose.

MODE FOR INVENTION

The present invention will now be described in more detail. Disclosures that are not included herein will be readily recognized and appreciated by those skilled in the art, and thus their description is omitted.

1. COMPARATIVE EXAMPLES: PRODUCTION OD D-PSICOSE ON ENZYMATIC CONVERSION

Comparative Example 1

An enzymatic conversion reaction was carried out using *Corynebacterium glutamicum* (KCCM11403P), which is a recombinant strain known to express a variant of a psicose epimerase derived from *Agrobacterium tumefaciens* (see Korean Patent No. 10-1455759). 0.1 M D-fructose was dissolved in water and 10 mM MnCl$_2$ was added thereto to prepare a raw material for enzymatic conversion reaction. The strain (20% w/w) was added to the raw material and the reaction was allowed to proceed at pH 8.0 and 55° C. for 3 h.

Thereafter, HPLC analysis was performed by loading the sample onto an Aminex HPX-87C column (Bio-Rad) at 80° C. and allowing water as a mobile phase to flow at a rate of 0.6 ml/min through the column. The areas under the peaks corresponding to the substrate (D-fructose) of the psicose epimerase and the product (D-psicose) were compared and quantified to calculate conversion rate of D-fructose.

As a result, the conversion rate to D-psicose by the enzymatic conversion method was 25% (Table 1).

Comparative Example 2

An enzymatic conversion reaction was carried out using a psicose epimerase derived from *Kaistia granuli*. The enzyme was produced by the following procedure. First, 5 ml of LB-ampicillin medium (Difco) was inoculated with recombinant strain (*E. coli* BL21(DE3)/KGDPE (KCCM11918P) expressing the psicose epimerase of SEQ ID NO: 4. The inoculum was cultured in an incubator at 37° C. until an absorbance of 1.5 at 600 nm was reached. 500 ml of LB-ampicillin medium was inoculated with the culture broth, followed by main culture. When the absorbance of the culture at 600 nm reached 0.7, 0.5 mM IPTG was added to induce mass expression of the D-psicose 3-epimerase. Culture was continued at a temperature of 16° C. with stirring at 150 rpm for 16 h. In order to purify enzyme, the culture broth was centrifuged at 8000 rpm for 20 min to collect bacterial cells. The collected bacterial cells were washed twice with 0.85% (w/v) NaCl, suspended in a lysis buffer (50 mM Tris-HCl, pH 7.0, 300 mM NaCl), and disrupted at 4° C. for 20 min using an ultrasonic homogenizer. The cell lysate was centrifuged at 13,000 rpm and 4° C. for 20 min. The supernatant was collected, loaded onto a Ni-NTA Superflow column (Qiagen) pre-equilibrated with the lysis buffer. A buffer (50 mM Tris-HCl, 300 mM NaCl, pH 7.0) containing 20 mM imidazole and a buffer (50 mM Tris-HCl, 300 mM NaCl, pH 7.0) containing 250 mM imidazole were allowed to flow sequentially through the column. The monomer of the enzyme was found to have a molecular weight of ~32 kDa, as determined by SDS-PAGE.

0.1 M D-fructose was dissolved in water and 10 mM $MnCl_2$ was added thereto to prepare an enzyme reaction solution for enzymatic conversion reaction. To the enzyme at higher concentrations of 1.7 M and 2.8 M in the presence of sodium aluminate were 268% and 212% higher than in Comparative Example 1, respectively, indicating that the addition of the aluminate significantly increases the conversion rate to D-psicose (see (a) to (c) of FIG. 1 and (a) of FIG. 3).

Example 1-2

50 mM sodium aluminate ($NaAlO_2$) was added to the enzyme reaction solution containing 0.1 M D-fructose prepared in Comparative Example 2. D-fructose was converted to D-psicose under the same conditions as described in Comparative Example 2. The conversion rate of D-fructose was analyzed in the same manner as described in Comparative Example 2.

The results are shown in Table 1. As can be seen from Table 1, the conversion rate of D-fructose in the presence of sodium aluminate was 200% higher than in Comparative Example 1, indicating that the addition of the aluminate significantly increases the conversion rate to D-psicose as in Example 1-1 (see (d) of FIG. 1 and (b) of FIG. 3).

TABLE 1

|  | Comparative Example 1 | Comparative Example 2 | Example 1-1 | | | Example 1-2 |
|---|---|---|---|---|---|---|
| D-fructose concentration (M) | 0.1 | 0.1 | 0.1 | 1.7 | 2.8 | 0.1 |
| Salt concentration (M) | 0 | 0 | 0.05 | 0.85 | 1.4 | 0.05 |
| Molar concentration ratio | — | — | 0.5 | 0.5 | 0.5 | 0.5 |
| Amount of D-fructose added (g/L) | 18 | 18 | 18 | 300 | 500 | 18 |
| Amount of D-psicose produced (g/L) | 4.5 | 4.5 | 12 | 201 | 265 | 9 |
| Conversion rate (%) | 25 | 25 | 67 | 67 | 53 | 50 |
| Relative conversion rate (%) | — | — | 268 | 268 | 212 | 200 | reaction solution was added 0.4 mg/ml of the purified enzyme. The reaction was allowed to proceed at pH 8.0 and 55° C. for 3 h.

Thereafter, HPLC analysis was performed by loading the sample onto an Aminex HPX-87C column (Bio-Rad) at 80° C. and allowing water as a mobile phase to flow at a rate of 0.6 ml/min through the column. The areas under the peaks corresponding to the substrate (D-fructose) of the psicose epimerase and the product (D-psicose) were compared and quantified to calculate conversion rate of D-fructose.

As a result, the conversion rate to D-psicose by the enzymatic conversion method was 25% (Table 2).

2. EXAMPLE 1: PRODUCTION OF D-PSICOSE IN THE PRESENCE OF ALUMINATE

Example 1-1

Raw materials were prepared in the same manner as in Comparative Example 1, except that the concentration of D-fructose was changed to 0.1 M, 1.7 M, and 2.8 M. 0.05 M, 0.85 M, and 1.4 M sodium aluminate ($NaAlO_2$) were added to the raw materials containing 0.1 M, 1.7 M, and 2.8 M D-fructose, respectively. D-fructose was converted to D-psicose under the same conditions as described in Comparative Example 1. The conversion rates of D-fructose were analyzed in the same manner as described in Comparative Example 1.

The results are shown in Table 1. As can be seen from Table 1, the conversion rate of 0.1 M D-fructose in the presence of sodium aluminate was 268% higher than in Comparative Example 1. The conversion rates of D-fructose

3. EXAMPLE 2: PRODUCTION OF D-PSICOSE IN THE PRESENCE OF IODATE

Example 2-1

25 mM potassium iodate ($KIO_3$) was added to the raw material containing 0.1 M D-fructose prepared in Comparative Example 1. D-fructose was converted to D-psicose under the same conditions as described in Comparative Example 1. The conversion rate of D-fructose was analyzed in the same manner as described in Comparative Example 1.

Figure 1A:
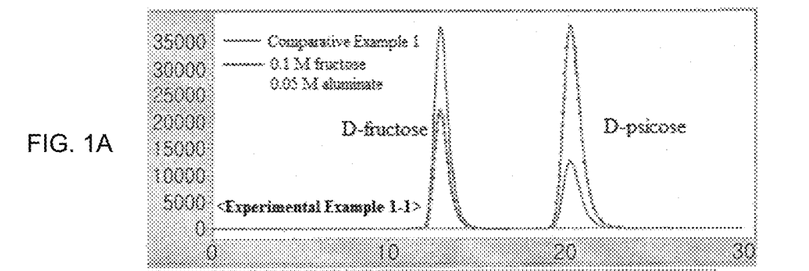
FIG. 1 shows HPLC chromatograms obtained when D-fructose was converted to D-psicose using a D-psicose 3-epimerase in Comparative Example 1 and when D-fructose was converted to D-psicose using a D-psicose 3-epimerase in the presence of an aluminate in Example 1-1 ((a) 0.1 M D-fructose, (b) 1.7 M D-fructose, and (c) 2.8 M D-fructose) and Example 1-2 (d).
Figure 1B:
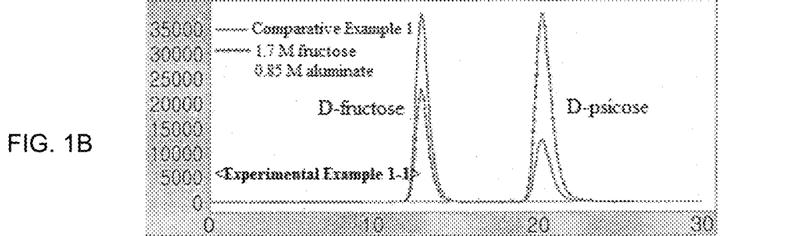
Figure 1C:
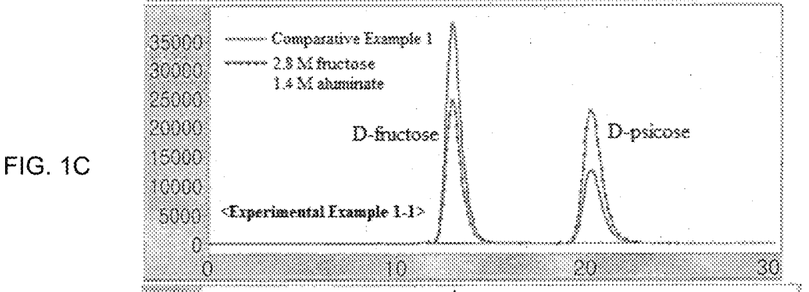
Figure 1D:
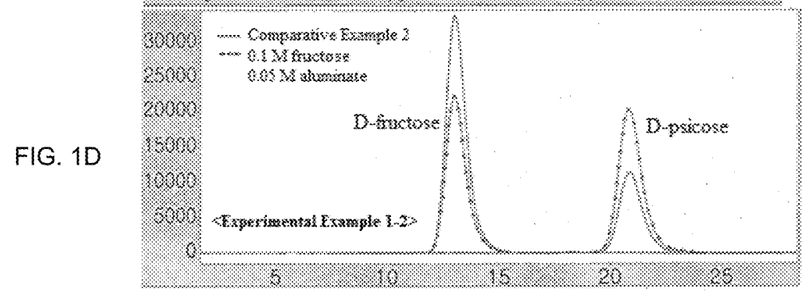
Figure 2A:
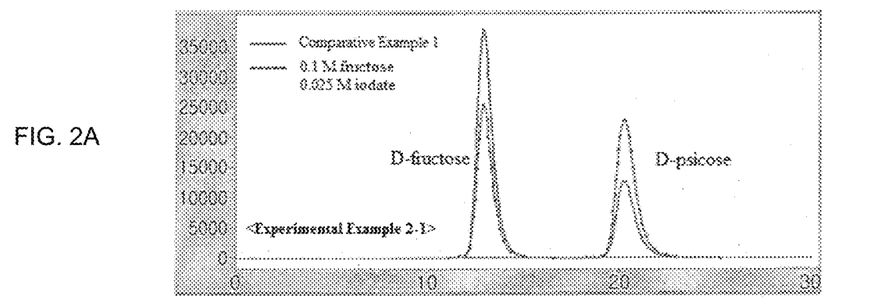
FIG. 2 shows HPLC chromatograms obtained when D-fructose was converted to D-psicose using a D-psicose 3-epimerase in Comparative Example 2 and when D-fructose was converted to D-psicose using a D-psicose 3-epimerase in the presence of an iodate in Example 2-1 (a) and Example 2-2 (b).
Figure 2B:
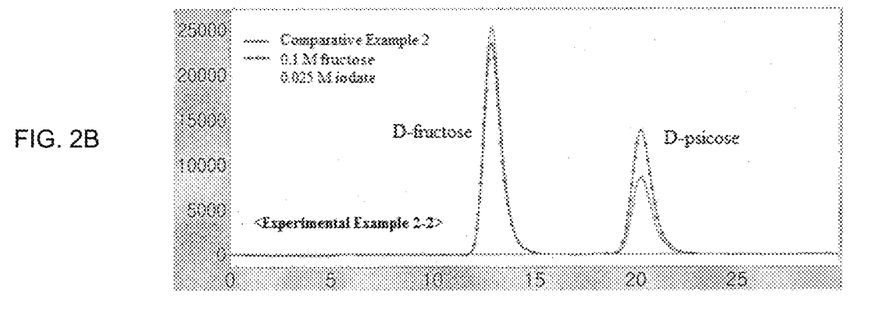
Figure 3A:
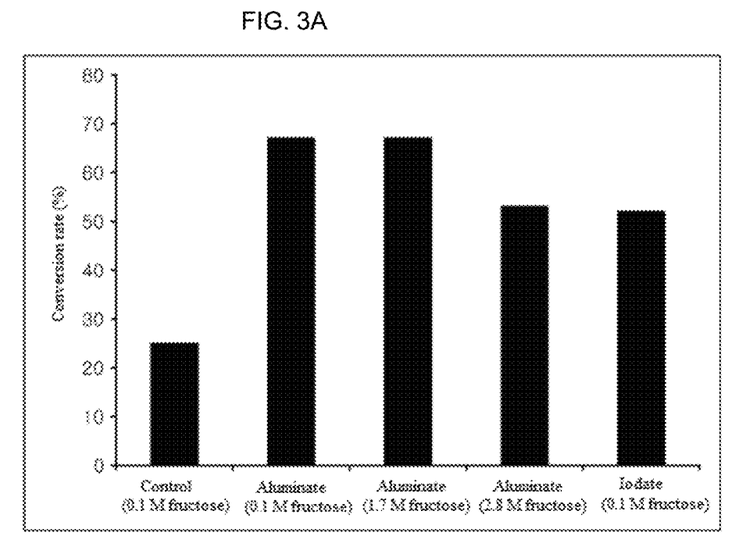
FIG. 3 shows the conversion rates (%) of D-fructose to D-psicose using a D-psicose 3-epimerase in Comparative Example 1 and Examples 1-1 and 2-1 (a) and in Comparative Example 2 and Examples 1-2 and 2-2 (b).
Figure 3B:
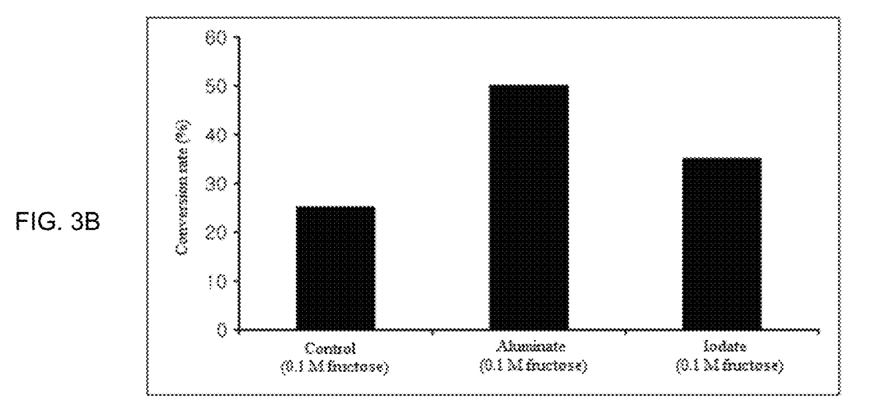
Figure 4:
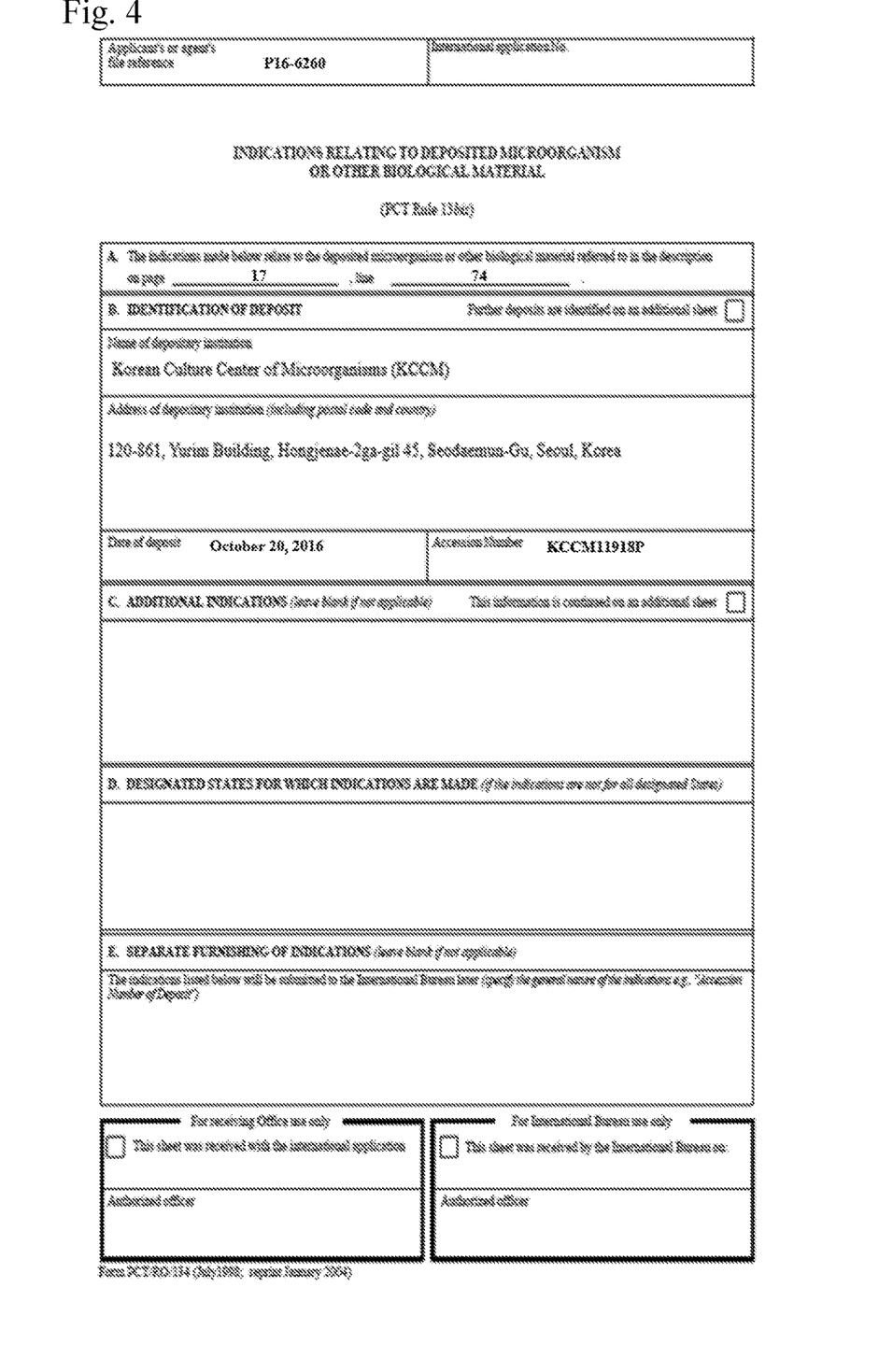
FIG. 4 is Form PCT/RO/134 showing indications relating to deposited microorganism or other biological material.

As can be seen from Table 2, the conversion rate of D-fructose in the presence of potassium iodate was 208% higher than in Comparative Example 1, indicating that the addition of the iodate significantly increases the conversion rate to D-psicose (see (a) of FIG. 2 and (a) of FIG. 3).

Example 2-2

25 mM potassium iodate ($KIO_3$) was added to the raw material containing 0.1 M D-fructose prepared in Comparative Example 2. D-fructose was converted to D-psicose under the same conditions as described in Comparative Example 1. The conversion rate of fructose was analyzed in the same manner as described in Comparative Example 1.

As can be seen from Table 2, the conversion rate of D-fructose in the presence of potassium iodate was 140% higher than in Comparative Example 1, indicating that the addition of the iodate significantly increases the conversion rate to D-psicose (see (b) of FIG. 2 and (b) of FIG. 3).

TABLE 2

|  | Comparative Example 1 | Comparative Example 2 | Example 2-1 | Example 2-2 |
|---|---|---|---|---|
| D-fructose concentration (M) | 0.1 | 0.1 | 0.1 | 0.1 |
| Salt concentration (M) | 0 | 0 | 0.025 | 0.025 |
| Molar concentration ratio | — | — | 0.25 | 0.25 |
| Amount of D-fructose added (g/L) | 18 | 18 | 18 | 18 |
| Amount of D-psicose produced (g/L) | 4.5 | 4.5 | 9.3 | 6.3 |
| Conversion rate (%) | 25 | 25 | 52 | 35 |
| Relative conversion rate (%) | — | — | 208 | 140 |

Although the particulars of the present invention have been described in detail, it will be obvious to those skilled in the art that such particulars are merely preferred embodiments and are not intended to limit the scope of the present invention. Therefore, the actual scope of the present invention is defined by the appended claims and their equivalents.

The invention claimed is:

1. A composition for producing D-psicose, comprising (a) a D-psicose 3-epimerase, a microorganism expressing a D-psicose 3-epimerase or a culture of a microorganism expressing a D-psicose 3-epimerase and (b) at least one salt selected from the group consisting of aluminates and iodates.

2. The composition according to claim 1, further comprising D-fructose.

3. A method for producing D-psicose from D-fructose, comprising adding at least one salt selected from the group consisting of aluminates and iodates to a D-psicose 3-epimerase, a microorganism expressing a D-psicose 3-epimerase or a culture of a microorganism expressing a D-psicose 3-epimerase, and adding D-fructose before, after, or simultaneously with the addition of the salt.

4. A method for increasing the conversion rate of D-fructose to D-psicose using a D-psicose 3-epimerase, comprising adding at least one salt selected from the group consisting of aluminates and iodates to a D-psicose 3-epimerase, a microorganism expressing a D-psicose 3-epimerase or a culture of a microorganism expressing a D-psicose 3-epimerase, and adding D-fructose before, after, or simultaneously with the addition of the salt.

* * * * *

SEQUENCE LISTING

<160> NUMBER OF SEQ ID NOS: 4

<210> SEQ ID NO 1
<211> LENGTH: 289
<212> TYPE: PRT
<213> ORGANISM: Artificial Sequence
<220> FEATURE:
<223> OTHER INFORMATION: Amino acid sequences of the triple-mutant from D-psicose 3-epimerase

<400> SEQUENCE: 1

```
Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
            20                  25                  30

Leu Glu Val Ala Ala His His Ile Asn Glu Tyr Ser Asp Ala Glu Leu
        35                  40                  45

Ala Thr Ile Arg Lys Ser Ala Lys Asp Asn Gly Ile Ile Leu Thr Ala
    50                  55                  60

Gly Ile Gly Pro Ser Lys Thr Lys Asn Leu Ser Ser Pro Asp Ala Ala
65                  70                  75                  80

Val Arg Ala Ala Gly Lys Ala Phe Phe Glu Arg Thr Leu Ser Asn Val
                85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
        115                 120                 125

Gly Val Glu Gly Ile Asn Gly Ile Ala Asp Phe Ala Asn Asp Leu Gly
    130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Cys Asn Arg Arg Val Pro Gly Lys Gly Arg Met Pro
    210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
```

```
                        245                 250                 255
Ile Lys Val Trp Arg Asp Leu Ser Gly Gly Ala Asp Ile Ala Lys Met
                260                 265                 270

Asp Glu Asp Ala Arg Asn Ala Leu Ala Phe Ser Arg Phe Val Leu Gly
            275                 280                 285

Gly

<210> SEQ ID NO 2
<211> LENGTH: 289
<212> TYPE: PRT
<213> ORGANISM: Artificial Sequence
<220> FEATURE:
<223> OTHER INFORMATION: Amino acid sequence of the double-mutant from
      D-psicose 3-epimerase

<400> SEQUENCE: 2

Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
                20                  25                  30

Leu Glu Val Ala Ala His His Ile Asn Glu Tyr Ser Asp Ala Glu Leu
            35                  40                  45

Ala Thr Ile Arg Lys Ser Ala Lys Asp Asn Gly Ile Ile Leu Thr Ala
        50                  55                  60

Gly Ile Gly Pro Ser Lys Thr Lys Asn Leu Ser Ser Glu Asp Ala Ala
65                  70                  75                  80

Val Arg Ala Ala Gly Lys Ala Phe Phe Glu Arg Thr Leu Ser Asn Val
                85                  90                  95

Ala Lys Leu Asp Ile His Thr Ile Gly Gly Ala Leu His Ser Tyr Trp
            100                 105                 110

Pro Ile Asp Tyr Ser Gln Pro Val Asp Lys Ala Gly Asp Tyr Ala Arg
        115                 120                 125

Gly Val Glu Gly Ile Asn Gly Ile Ala Asp Phe Ala Asn Asp Leu Gly
130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
            180                 185                 190

Ser Phe Gly Asp Ala Ile Arg Thr Ala Gly Pro Leu Leu Gly His Phe
        195                 200                 205

His Thr Gly Glu Cys Asn Arg Arg Val Pro Gly Lys Gly Arg Met Pro
210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
            260                 265                 270

Asp Glu Asp Ala Arg Asn Ala Leu Ala Phe Ser Arg Phe Val Leu Gly
        275                 280                 285

Gly

<210> SEQ ID NO 3
```

<211> LENGTH: 289
<212> TYPE: PRT
<213> ORGANISM: Unknown
<220> FEATURE:
<223> OTHER INFORMATION: Agrobacterium tumefaciens

<400> SEQUENCE: 3

Met Lys His Gly Ile Tyr Tyr Ser Tyr Trp Glu His Glu Trp Ser Ala
1               5                   10                  15

Lys Phe Gly Pro Tyr Ile Glu Lys Val Ala Lys Leu Gly Phe Asp Ile
                20                  25                  30

Ile Glu Val Ala Ala His His Ile Asn Glu Tyr Ser Asp Ala Glu Leu
            35                  40                  45

Ala Thr Ile Arg Lys Ser Ala Lys Asp Asn Gly Ile Ile Leu Thr Ala
        50                  55                  60

Gly Ile Gly Pro Ser Lys Thr Lys Asn Leu Ser Ser Gly Asp Ala Ala
65                  70                  75                  80

Val Arg Ala Ala Gly Lys Ala Phe Phe Glu Arg Thr Leu Ser Asn Val
                85                  90                  95

Ala Lys Leu Asp Ile His Thr Ile Gly Gly Ala Leu His Ser Tyr Trp
                100                 105                 110

Pro Ile Asp Tyr Ser Gln Pro Val Asp Lys Ala Gly Asp Tyr Ala Arg
            115                 120                 125

Gly Val Glu Gly Ile Asn Gly Ile Ala Asp Phe Ala Asn Asp Leu Gly
        130                 135                 140

Ile Asn Leu Cys Ile Glu Val Leu Asn Arg Phe Glu Asn His Val Leu
145                 150                 155                 160

Asn Thr Ala Ala Glu Gly Val Ala Phe Val Lys Asp Val Gly Lys Asn
                165                 170                 175

Asn Val Lys Val Met Leu Asp Thr Phe His Met Asn Ile Glu Glu Asp
                180                 185                 190

Ser Phe Gly Asp Ala Ile Arg Thr Ala Gly Pro Leu Leu Gly His Phe
            195                 200                 205

His Thr Gly Glu Ser Asn Arg Arg Val Pro Gly Lys Gly Arg Met Pro
        210                 215                 220

Trp His Glu Ile Gly Leu Ala Leu Arg Asp Ile Asn Tyr Thr Gly Ala
225                 230                 235                 240

Val Ile Met Glu Pro Phe Val Lys Thr Gly Gly Thr Ile Gly Ser Asp
                245                 250                 255

Ile Lys Val Trp Arg Asp Leu Ser Gly Gly Ala Asp Ile Ala Lys Met
                260                 265                 270

Asp Glu Asp Ala Arg Asn Ala Leu Ala Phe Ser Arg Phe Val Leu Gly
            275                 280                 285

Gly

<210> SEQ ID NO 4
<211> LENGTH: 297
<212> TYPE: PRT
<213> ORGANISM: Unknown
<220> FEATURE:
<223> OTHER INFORMATION: Kaistia granuli

<400> SEQUENCE: 4

Met Lys Asn Lys Leu Gly Val His Ala Gln Val Trp Val Gly Gly Trp
1               5                   10                  15

Ser His Ala Glu Ala Glu Arg Ala Ile Ala Ser Thr Ala Ser Leu Gly
                20                  25                  30

```
Tyr Asp Tyr Ile Glu Ala Pro Ala Leu Asp Pro Ser Leu Ile Asp Ile
    35              40              45
Asp Phe Thr Arg Lys Ala Leu Glu Lys His Gly Leu Gly Ile Thr Thr
    50              55              60
Ser Leu Gly Leu Asp Asp Ser Cys Asp Ile Ser Ser Gly Asp Pro Asp
65              70              75              80
Lys Lys Ala Arg Gly Gln Ala His Leu Met Lys Val Val Ser Thr Thr
            85              90              95
Arg Asp Leu Gly Gly Thr His Ile Thr Gly Ile Leu Tyr Ser Gly Phe
            100             105             110
Gln Lys Tyr Phe Thr Pro Ala Thr Pro Glu Gly Val Ala Gly Ala Val
            115             120             125
Glu Val Leu His His Val Ala Glu Glu Ala Ala Lys Ser Asn Ile Thr
            130             135             140
Leu Gly Leu Glu Val Val Asn Arg Tyr Glu Thr Asn Val Ile Asn Thr
145             150             155             160
Ala Ala Gln Gly Val Glu Leu Cys Lys Arg Val Gly Met Pro Asn Val
            165             170             175
Lys Val His Leu Asp Cys Tyr His Met Asn Ile Glu Glu Ala Asp Ala
            180             185             190
Glu Arg Ala Ile Ile Asp Thr Gly Asp Tyr Leu Gly Tyr Phe His Thr
            195             200             205
Gly Glu Ser His Arg Gly Tyr Leu Gly Thr Gly Ser Ile Asp Phe Thr
            210             215             220
Arg Ile Phe Arg Gly Leu Val Lys Ala Asn Tyr Gln Gly Pro Ile Cys
225             230             235             240
Phe Glu Ser Phe Ser Ser Ala Val Ala Gly Glu Pro Leu Ser Gly Ile
            245             250             255
Leu Gly Ile Trp Arg Asn Leu Trp Thr Asp Ser Thr Asp Leu Cys Arg
            260             265             270
His Ala Met Gln Phe Thr Gln Ala Gln Met Gln Ala Ala Glu Gln Ala
            275             280             285
Gln Ser Ile Arg Thr Gly Ala Asp Trp
290             295
```